United States Patent [19]

Neefe

[11] 4,401,371
[45] * Aug. 30, 1983

[54] HYDROGEL OXYGEN GENERATOR WITH IMPROVED FLUID FLOW

[76] Inventor: Charles W. Neefe, P.O. Box 429, Big Spring, Tex. 79720

[*] Notice: The portion of the term of this patent subsequent to May 19, 1998 has been disclaimed.

[21] Appl. No.: 98,669

[22] Filed: Oct. 25, 1980

Related U.S. Application Data

[63] Continuation-in-part of Ser. No. 78,171, Sep. 24, 1979, Pat. No. 4,268,132.

[51] Int. Cl.³ .............................................. G02C 7/04
[52] U.S. Cl. ............................. 351/160 R; 351/160 H
[58] Field of Search ........................ 351/160 H, 160 R

[56] References Cited

U.S. PATENT DOCUMENTS 4,268,132  5/1981  Naafa ............................. 351/160 H

FOREIGN PATENT DOCUMENTS 2519708  11/1975  Fed. Rep. of Germany ... 351/160 R
2248527   5/1975  France ........................... 351/160 R Primary Examiner—John K. Corbin
Assistant Examiner—Scott J. Sugarman

[57] ABSTRACT

A contact lens concave-convex in form made of a transparent, optically clear hydrogel polymer containing micro-photoelectrolysis elements to produce hydrogen and oxygen by the electrolysis of water and capillary tubes within the hydrogel polymer to remove the hydrogen and oxygen from the lens and supplying water for electrolysis.

6 Claims, 2 Drawing Figures

HYDROGEL OXYGEN GENERATOR WITH IMPROVED FLUID FLOW

This is a continuation in part of application Ser. No. 78,171 filed Sept. 24, 1979 by Charles W. Neefe, entitled "Oxygen Generating Contact Lens" now U.S. Pat. No. 4,268,132 issued May 19, 1981.

THE PRIOR ART

Contact lenses that are being used at this time depend upon the flow of lachrymal fluids around the edge of the lens to supply the cornea with its necessary oxygen. The cornea tissue maintains a temperature much lower than the other body tissues. This is due to evaporation at the corneal surface and the lack of blood supply to the cornea which warms the rest of the body. The temperature of the cornea must be at this lower level or its metabolic processes will be accelerated. The plastic now being used for fabricating material covering a large percent of the corneal area, raises its temperature which increases the chemical activity of the metabolic processes and therefore the cornea demands more oxygen to maintain normal metabolism. The present lenses preclude the free exchange of atmospheric oxygen dissolved in the precorneal fluid from reaching the corneal tissue. The result is edema and epithelium disorganization.

Lenses have been made with small holes drilled through the lens in an effort to overcome this problem. If the holes are large, they will be seen by the wearer, and if small enough not to be seen, they become clogged with body secretions and are rendered useless.

Silicone and other highly permeable materials are capable of oxygen enrichment if the material has a higher permeability to oxygen than to nitrogen or carbon dioxide.

Present corneal contact lenses must be fitted with the peripheral zone flatter than the cornea in order to provide lachrymal flow and oxygen to the apex of the cornea. This clearance created around the edge allows the lens to move about the cornea and may be forced off center by the action of the upper lid; also lid sensation and discomfort result from edge stand off. With the present corneal contact lenses, no fixed alignment between the optical center of the contact lens and eye is possible.

This new lens design may be employed as a therapeutic device by adding the required medication to the lens material. The medication will be dissolved slowly by the lachrymal fluids and find its way to the corneal tissue by diffusion to the surface of the lens. Since this lens does not need to be removed, long-lasting and highly effective medications are now possible.

SUMMARY OF THE INVENTION

Figure 1:
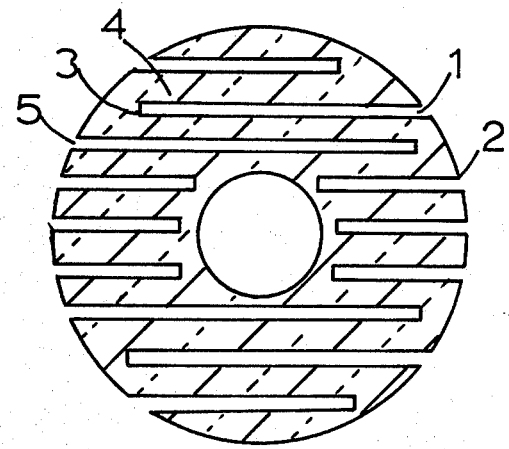
FIG. 1 shows the micro-tubes intersecting only one edge of the hydrogel.

Natural photosynthesis provides the most obvious example of photochemical solar energy conversion. Field efficiency (yearly average, best crops and so on) is about 1%. These figures are not so high as the efficiency for electricity generation by solid-state photovoltaics. Sunlight-induced photoelectrolysis conversion of water to hydrogen and oxygen approaches the field efficiency of natural photosynthesis. Solid-state photovoltaic devices are the only man-made systems having any wide spread use for solar energy conversion based on electronic excitations. Solid/liquid junction devices represent the best chemical systems for converting light energy to hydrogen and oxygen from water. The most impressive systems for solar energy conversion to electricity and production of oxygen from water involve the interfacial photoredox events at the junction between semiconductors and liquid electrolyte solutions. Semiconductor/liquid junction cells are different from photogalvanic cells in that light is absorbed by a solid electrode, not by electrolyte species in solution. Two of the most efficient systems for the photoelectrolysis of water is the strontium titanium trioxide based cell and gallium arsinide cells. The overall efficiency of converting solar energy to hydrogen and oxygen is about 1%. N-type titanium dioxide/p-type gallium phosphorus based cells produce hydrogen and oxygen with no other energy input that the light striking the two electrodes. This type of observation led to the conclusion that "photochemical diodes" consisting of aqueous suspensions of n-type titanium dioxide/p-type gallium phosphorus particles can yield hydrogen and oxygen from water on optical excitation. Another approach is to sensitize stable semiconductors using visible-light-absorbing dyes attached to the surface. In this approach the aim is to absorb light by a dye layer on the semiconductor surface to produce an excited state; this has been achieved by using zinc oxide sensitized with rose bengal.

The oxygen consumption rate of the human cornea is approximated to be 2.8 ml/cm$^2$-24 hrs. This value has been determined by Jauregui and Fatt, "Estimation of the Vivo Oxygen Consumption of the Human Corneal Epithelium", in the American Journal of Optometry and Archives of American Academy of Optometry, June 1972, page 507.

The carrier or lens material may be any hydrogel water containing material. Examples of carrier materials are poly hydroxyethyl methacrylate, poly hydroxypropyl methacrylate, and hydratable polymethylmethacrylate.

Photosensitive particles are suspended in the monomers and a suitable catalyst is added to achieve polymerization. The photosensitive particles are selected from titanium dioxide combined with gallium phosphorus; platinum combined with strontium titanium trioxide, tin oxide combined with a dye; or zinc oxide combined with rose bengal dye. Ferric oxide, titanium dioxide, tin oxide and zinc oxide photoanodes may be used in combination with a noble metal such as platinum. After polymerization, the lens polymer containing the photosensitive particles imbedded in the periphery are machined into contact lenses having a clear transparent central area and micro-photosensitive particles surrounding the central optical zone of the lens. After hydration, the liquid semiconductor junction is established at the photosensitive interface and hydrogen and oxygen will be released by the electrolysis of water upon exposure to light.

The rate at which gases are generated must not exceed the solubility limits of the water contained within the lens matrix. Therefore, the efficiency of the photosensitive particles must be kept low to prevent bubbles from forming. The oxygen requirements of the cornea are very low compared to the quantities of oxygen available from the photoelectrochemical decomposition of water. Therefore, a surplus of dissolved oxygen will be available for storage in the lens structure to provide the oxygen requirements of the cornea during sleep.

Figure 2:
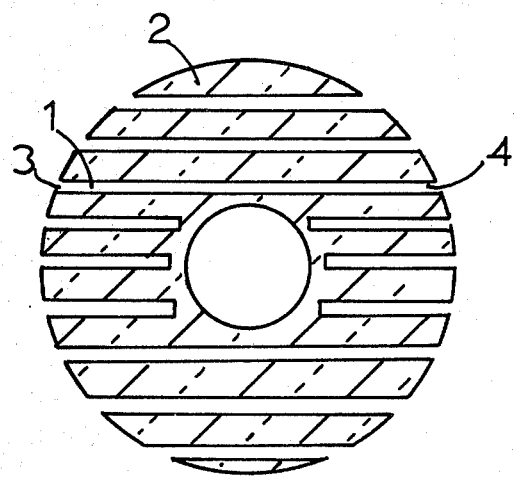
FIG. 2 shows the micro-tubes passing through the hydrogel.

Micro-capillary tubes ranging in diameter from 0.001 m/m to 1.0 m/m may be incorporated in the hydrogel structure. These tubes, 1 FIGS. 1 and 2, may be connected to either surface or to any side of the structure, 1 FIG. 1, or they preferably may pass completely through the hydrogel, 1 FIG. 2. FIG. 1 shows the tubes in contact with one edge of the hydrogel, 2 FIG. 1, and deadening within the hydrogel, 3 FIG. 1. The fluid within the inlet tube, 5 FIG. 1, must pass through the hydrogel material, 4 FIG. 1, to reach the outlet tube, 1 FIG. 1. FIG. 2 shows the tubes, 1 FIG. 2, passing completely through the hydrogel, 2 FIG. 2. The inlet port, 3 FIG. 2, and outlet port, 4 FIG. 2, are connected by the continuous tube, 1 FIG. 2. The presence of these tubes provides for faster exchange of the electrolyte and increased production of hydrogen and oxygen. The tubes are formed by imbedding a fiber within the monomer before polymerization and dissolving the fibers from the polymerized material. Glass fibers may be imbedded and later removed with hydrofluoric acid after the polymer is formed to create the micro-tubes. For contact lenses these tubes must be kept well outside the central optical zone. For other applications such as the production of hydrogen and oxygen for fuel, the tubes occupy the entire area of the hydrogel.

A sulfonate or a phosphorus group may be incorporated in the polymer matrix to increase the mobility of the water and prevent fouling of the exterior surface. Fouling of the surface of the photosensitive particles by debris is prevented by the presence of the hydrogel matrix which completely surrounds it. Most debris particles are hydrophobic, or in other words, repel water; most of them also bear a negative electric charge. The most serious debris problems are caused by materials such as oily particles and proteins, which have large surface areas that are hydrophobic, or in other words repel water. When a hydrophobic substance is in an aqueous environment, it can reduce its total energy by reducing the area exposed to the water; two hydrophobic particles tend to clump together expelling the water from the space between them and thereby reducing their exposed surface. This phenomena is called hydrophobic bonding. In the same way such a particle can be held to the surface of a contact lens by the elimination of repulsive interactions with the surrounding water. Most of the debris materials also bear a negative electric charge and hydrogen bonding involving these charges also contribute to the buildup of debris. In this kind of bonding the slight positive charge of hydrogen atom at the surface of the lens attracts a negatively charged group in the debris particle.

In liquid water about half the molecules at any moment are in clusters that have the same orderly structure as a crystal of ice. In the clusters, each water molecule is placed so that the oxygen atom occupies the vertex of a tetrahedron and so that a hydrogen bond connects each pair of water molecules. In ice, this stable structure extends over a long distance, but in the liquid state the icelike clusters generally include only a few molecules each, and they are constantly forming and disintegrating. Inside the structure of a negative charged hydrophilic soft lens, the water assumes an icelike state, in which the molecules have an orderly arrangement and are held together by hydrogen bonds. The geometry of the icelike state is tetrahedral, with each oxygen atom surrounded by four others at equal distances. Other molecules and particles are rejected, including not only those that are too large to fit through the lens membrane but also small molecules that cannot conform to the icelike structure. Ions in particular are excluded because they are shielded by a layer of water that would disrupt the icelike lattice. In the production of hydrogen and oxygen for fuels, this ability to control the presence of ions and catalysts at the reactive site is a tremendous asset. With the ability to control the flow of ions, catalysts and dissolved gases, it is possible to produce carbohydrates from water and dissolved carbon dioxide with the energy for the uphill reaction supplied by light and the photosensitive materials imbedded within a water containing polymer. For contact lenses it is desirable to exclude all possible ions and provide only water within the lens structure. Therefore, the materials have the highest contact angle are selected for the lens membrane.

The liquid/solid junction is made with the electrolyte contained within the matrix of the polymer material. This provides unique conditions of self regulation and supplying a permanent, contamination free, liquid to solid interface. These properties separate or together offer many improvements in other applications of solar energy. Self regulation occurs when $O_2$ or $H_2$ are produced at a rate greater than the migration rate into the polymer matrix away from the reaction site where the gases are formed. When a layer of undissolved gas accumulates on the surface of the reaction site; the water is displaced and further gas production stops until the gas dissolves or is free to migrate into the micro-tubes and is conducted to the surface of the polymer.

DESCRIPTION OF THE PREFERRED EMBODIMENT

Photosensitive particles are mixed with the monomer hydroxyethyl methacrylate, 2% of the crosslinkers ethylene dimethacrylate and 0.25% of the catalyst 2,2$^1$Azobis (2 methylpropionitrite), the mixture is purged of oxygen, glass fibers are suitably placed within a mold around a clear cylinder of the same polymer mixture containing no fibers or photosensitive particles and the mold filled with the liquid monomer containing the photosensitive particles, the mold is placed under a nitrogen blanket and heated to 55° C. for twelve hours and post cured for 8 hours at 70° C. Contact lenses of concave-convex form having a clear optical zone formed by the clear cylinder free of tubes and photosensitive particles are then fabricated from the material. The glass fibers are removed by being dissolved with hydrofluoric acid, and the lens is hydrated in normal saline. When the lens is exposed to light, an electric potential will be present across the junction and oxygen will be released from the strantium titanium trioxide surface. The water present within the hydrophilic lens material acts as the required electrolyte and as a reservoir for the dissolved oxygen which may move through the lens material into the capillary tubes by diffusion and from the lens by way of the micro-capillary tubes.

Various modifications of course, can be made without departing from the spirit of this invention or the scope of the appended claims. It is understood that many variations are obtainable which will yield results as disclosed herein. The constants set forth in this disclosure are given as examples and are in no way final or binding.

I claim:

1. An oxygen and hydrogen generator comprising a water containing polymer having a plurality of photosensitive particles imbedded within the polymer which produce both hydrogen and oxygen by the photoelectrolysis of water when the photosensitive particles are excited by being exposed to light, said polymer having a plurality of open ended tubes extending into the polymer structure whereby the generated oxygen and hydrogen may pass within the tubes to the polymer surface.

2. A generator as in claim 1 wherein the polymer surface has a negative charge.

3. A generator as in claim 1 wherein the polymer surface is hydrophilic.

4. A generator as in claim 1 wherein the polymer surface is hydrophobic.

5. A generator as in claim 1 which is shaped into a contact lens and provides oxygen to the cornea of the eye.

6. A generator as in claim 1 wherein the generated oxygen is collected.

* * * * *